(12) United States Patent
Landis

(10) Patent No.: US 7,320,404 B2
(45) Date of Patent: Jan. 22, 2008

(54) MEDICAL PACKAGING

(75) Inventor: Larry R. Landis, Warsaw, IN (US)

(73) Assignee: Zimmer Technology, Inc., Warsaw, IN (US)

(*) Notice: Subject to any disclaimer, the term of this patent is extended or adjusted under 35 U.S.C. 154(b) by 323 days.

(21) Appl. No.: 11/201,032

(22) Filed: Aug. 10, 2005

(65) Prior Publication Data
US 2007/0034538 A1   Feb. 15, 2007

(51) Int. Cl.
*B65D 85/30* (2006.01)

(52) U.S. Cl. .................................. 206/438; 206/592

(58) Field of Classification Search ................ 206/438, 206/210, 521, 591, 592, 594, 440, 63.5
See application file for complete search history.

(56) References Cited

U.S. PATENT DOCUMENTS

| | | |
|---|---|---|
| 3,013,656 A | 12/1961 | Murphy |
| 4,211,325 A | 7/1980 | Wright |
| 4,216,860 A | 8/1980 | Heimann |
| 4,697,703 A | 10/1987 | Will |
| 4,730,726 A | 3/1988 | Holzwarth |
| 5,090,571 A | 2/1992 | Walker |
| 5,148,920 A | 9/1992 | Walker |
| 5,669,506 A * | 9/1997 | Lofgren et al. ............ 206/583 |
| 2004/0112781 A1 * | 6/2004 | Hofverberg et al. ........ 206/438 |

* cited by examiner

*Primary Examiner*—Jacob K. Ackun, Jr.
(74) *Attorney, Agent, or Firm*—Baker & Daniels LLP

(57) ABSTRACT

A medical package is provided for protecting a medical item.

27 Claims, 3 Drawing Sheets

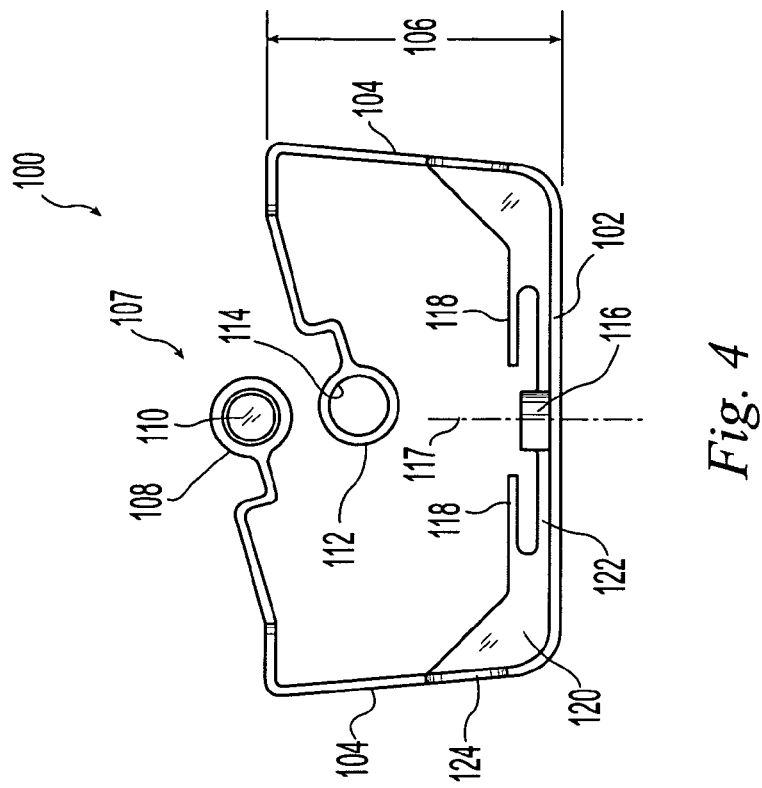
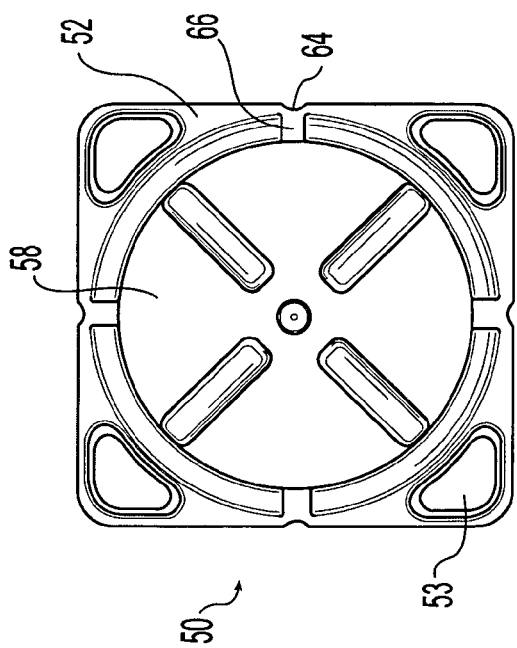
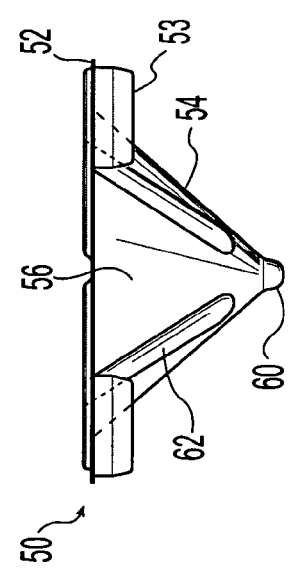

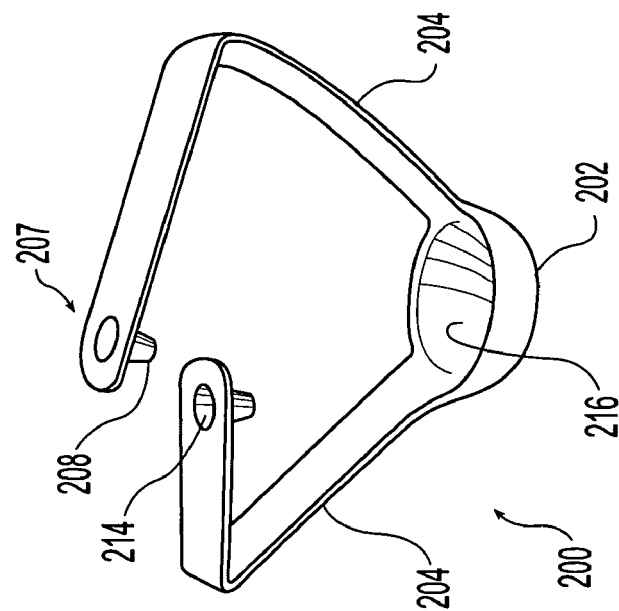
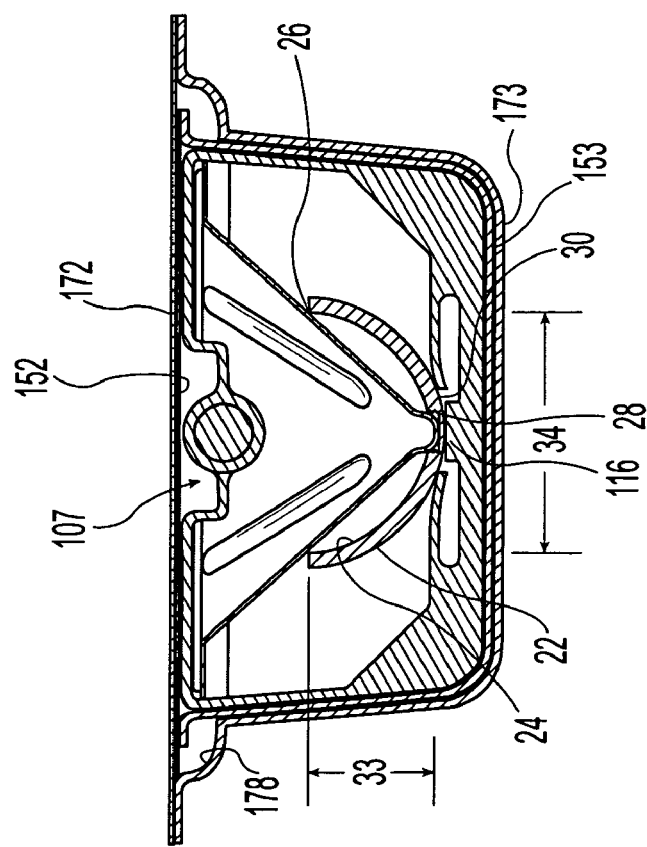

MEDICAL PACKAGING

FIELD OF THE INVENTION

The present invention relates to packages for medical devices.

BACKGROUND

The packaging of medical items intended for use in surgery frequently involves the use of a double sterile package, that is, an inner package containing the item and being sealed and sterilized and an outer package enclosing the inner package and also being sealed and sterilized. The item must be protected from damage and the integrity of the package seal must be protected to maintain sterility. To these ends, various package designs have been utilized to immobilize the item. With items such as hip and knee joint prostheses which are relatively heavy, the item must be firmly restrained against movement within the package. Furthermore, such items are available in a wide range of sizes such that the provision of suitable packaging can entail considerable expense in inventory and in the obtaining of regulatory approval for the packaging. At the point of use, the medical item should be readily removed from the package without risk of contamination or the need to manipulate cumbersome mechanisms that could lead to dropping of the item.

SUMMARY

The present invention provides a medical package for protecting a medical item.

In one aspect of the invention, a package for a medical device includes a container, an insert, and a retaining clip. The insert is releasably engaged with the medical device to constrain the position of the medical device relative to the insert. The retaining clip includes a base engaging the medical device and support arms extending from the base and encircling the insert to secure the insert in engagement with the medical device. The insert engages the container to constrain the position of the medical device relative to the container.

In another aspect of the invention, the insert, retaining clip, and medical device form a secure assembly insertable into and removable from the container as an assembled unit.

In another aspect of the invention, retaining clip further includes at least one spring engaged with the medical device to bias the medical device into contact with the insert.

In another aspect of the invention, the medical device has a height and a width and the insert includes a portion with a height and a width. The width of the portion varies along its height such that a single insert is interchangeably engageable with a plurality of different medical devices having different heights and widths.

In another aspect of the invention, the support arms are responsive to being squeezed by a users hand to elastically deform them from a first position in which the retaining clip secures the insert and medical device and a second position in which the insert and medical device may be inserted and removed from the retaining clip. The arms elastically return to the first position when they are no longer squeezed.

In another aspect of the invention, a package is provided for an acetabular shell component of a hip joint prosthesis. The shell has an outer surface, an inner surface, an equatorial opening and a polar hole communicating with the inner surface. The package includes a container, an insert, and a retaining clip. The insert has a top portion releasably engaged with the open top of the container and a projection extending downwardly from the top portion to engage the shell. The projection has an outer surface engaged with the equatorial opening and an end portion engaged with the polar hole. The retaining clip has a base supporting the shell and support arms extending upwardly from the base and encircling the insert to secure the insert in engagement with the shell.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2 is a top plan view of one component of the package of FIG. 1;

FIG. 3 is a side elevation view of the component of FIG. 2;

FIG. 4 is a side elevation view of another component of the package of FIG. 1;

FIG. 5 is a sectional view of the package of FIG. 1; and

FIG. 6 is an alternate arrangement for the component of FIG. 4.

DESCRIPTION OF THE ILLUSTRATIVE EXAMPLES

Figure 1:
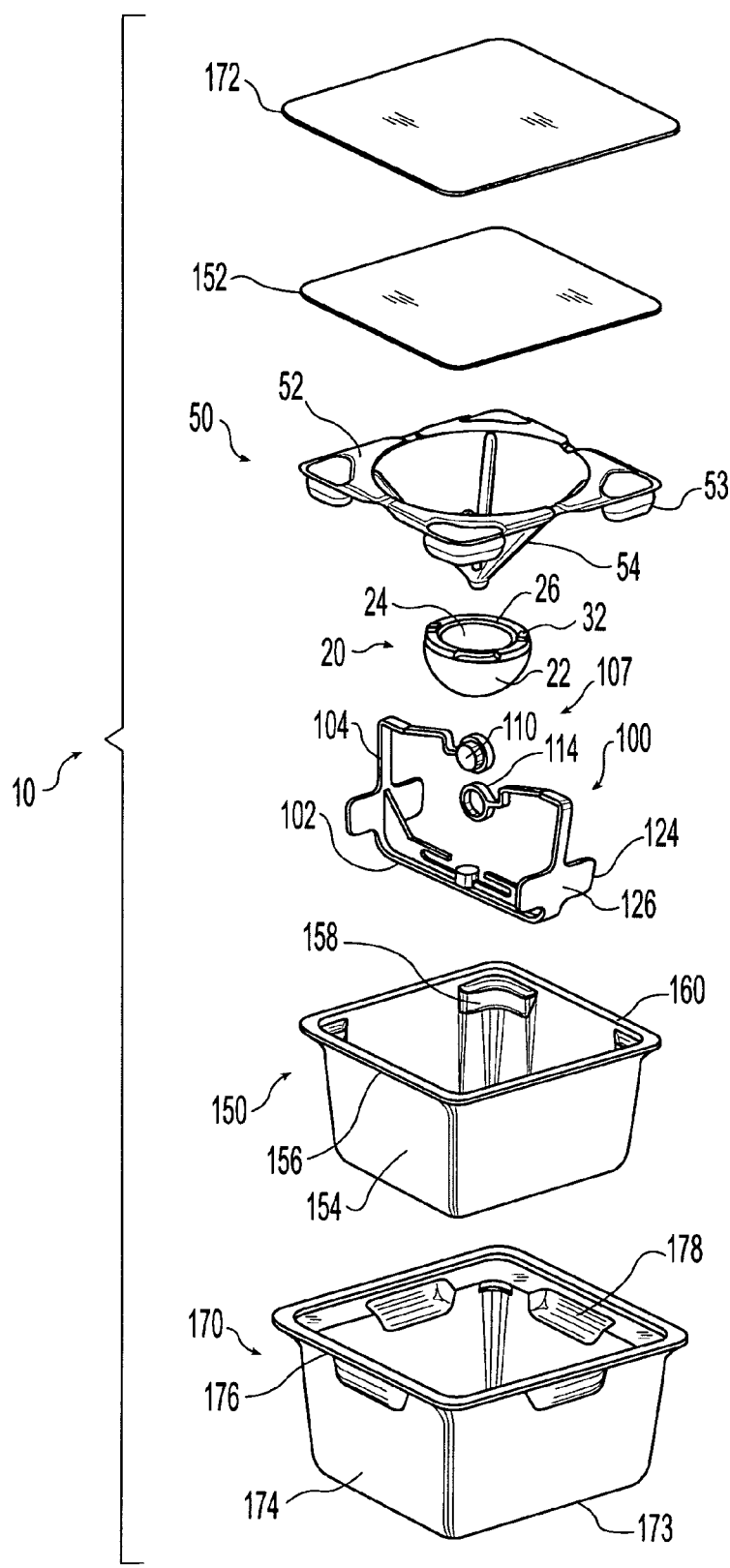
FIG. 1 is an exploded perspective view of an illustrative medical package according to the present invention.

Embodiments of a medical package include a two piece retainer for positioning a medical device within a container. The retainer includes an insert and a retaining clip. The insert may include a projection having a surface for engaging a portion of the device. The surface may define any suitable shape including cylindrical, spherical, conical, and/or other shapes. The surface may be shaped to engage differently sized devices at different locations on the surface. For example, a plurality of medical devices may have differing heights and widths and the projection may have a surface having a width that varies by height such that a single insert is interchangeably engageable with the plurality of devices. For example, an acetabular shell may be provided in a plurality of sizes wherein each size defines an equatorial opening having a width, or diameter, and a polar hole at a predetermined height above the polar hole. The insert may have an end portion for engaging the polar hole and a surface diameter that varies with height above the end portion to engage the equatorial openings of a plurality of differently sized shells. The surface may include projections and/or recesses for engaging and/or providing relief for features on the medical device. These projections and/or recesses may provide rotational constraint of the medical device relative to the insert. For example, the surface may include grooves for receiving tabs projecting from the medial device.

The retaining clip retains the engagement of the insert and medical device. The retaining clip may encircle the medical device and insert to hold them together. The retaining clip may provide a handle to facilitate gripping and manipulating the insert, medical device, and retaining clip assembly. The retaining clip may include a tensioning mechanism to tension the assembly to reduce the amount of relative motion between the insert, medical device, and retaining clip. The retaining clip may include a latch that permits the retaining clip to be assembled and removed from the insert and medical device in an unlatched condition and secures the retaining clip to the assembly in a latched condition. For example, the retaining clip may include a 360° band having one side separated into two halves of an interlocking latch. With the latch halves separated, the retaining clip may be opened to allow the insert and medical device to be placed within the confines of the band. The latch halves may then be fit together to secure the assembly. The retaining clip alternatively, or simultaneously, may be flexible between a condition in which the retaining clip secures the assembly and a condition in which the assembly may be disassembled to remove the medical device. For example, the retaining clip may include a 360° band that encircles the insert and medical device to secure the assembly. The band may be flexible such that squeezing opposite sides of the band causes it to bulge outwardly to permit the insert and medical device to be placed within and removed from the band. The retaining clip may define a handle to facilitate insertion and removal of the assembly from a container.

The container may be configured to receive the insert, medical device, and retaining clip assembly. The assembly may form a snap fit with the container. For example, the insert may include a top portion that engages the container opening in snap fitting relationship. A plurality of nesting containers may be included to provide a plurality of sterile barriers.

FIGS. 1-5 depict an illustrative embodiment of a medical package 10 for a medical device. The illustrative embodiment is configured for packaging an acetabular shell component 20 of a hip joint prosthesis. However, it is within the scope of the present invention for the package 10 to be configured for any medical device. The illustrative package 10 includes a two-piece retainer including an insert 50 and a retaining clip 100. The insert 50 engages the shell 20 and the retaining clip 100 encircles the insert and shell 20 to form an assembly that is easily inserted into and removed from a container. Preferably the container includes an inner container 150 that receives the retainer assembly and an outer container 170 that receives the inner container. Each of the containers 150, 170 is sealed with a sterile barrier lid 152, 172 such that the shell 20 is sealed in a double sterile package.

The exemplary medical device is a shell 20 having an outer spherical surface 22, an inner spherical surface 24, an equatorial opening 26, and a blind polar hole 28 formed partway from the inner surface 24 toward the outer surface 22 at the pole 30 of the component 20 (FIG. 5). The hole 28 is threaded to engage an insertion tool (not shown) to aid in manipulating the shell 20 during surgery. The exemplary shell 20 further includes a pair of tabs 32 projecting upwardly from the rim of the component 20 adjacent the opening 26 and positioned 180° apart. The tabs 32 engage a bearing liner (not shown) to prevent it from rotating relative to the shell 20 when the shell is implanted in a patient.

The insert 50 (FIGS. 2-3) is configured to engage the medical device. The insert 50 may be provided in different configurations for different medical devices such as different styles of shells 20, acetabular bearings, knee prostheses, and/or other medical devices. The illustrative insert 50 includes a rectangular top portion 52 and a shell engaging projection 54 extending downwardly from the top portion 52. The top portion 52 defines a square and includes snap lugs 53 extending downwardly from each corner. The projection 54 defines a hollow cone having an outer, shell engaging, surface 56 and an inner surface 58. The projection 54 terminates in an end portion 60 having a cylindrical side wall and a spherical tip. The outer surface 56 of the projection 54 includes elongated depressions 62, or grooves, for providing clearance relief and/or antirotation engagement of the shell 20. In the exemplary embodiment, the depressions 62 are formed into the outer surface 56 to receive the tabs 32 projecting upwardly from the rim of the shell 20. The insert may be made of any suitable material and formed by any suitable process. Preferably the insert is made of a lightweight, easily formed, polymer that can withstand common sterilization processes such as gamma irradiation and/or ethylene oxide exposure. Some exemplary materials include polyethylene terephthalate and high density polyethylene. The insert 50 may be formed by machining, injection molding, thermoforming, and/or other suitable processes. For example, the insert 50 may be economically thermoformed from a polyethylene terephthalate sheet over a plug in a vacuum forming chamber.

The outer surface 56 of the projection 54 engages the opening 26 of the shell 20 and the cylindrical end portion 60 of the projection 54 engages the polar hole 28 of the shell to stabilize the shell against side-to-side motion relative to the insert 50. For each size shell 20, there is a height 33 (FIG. 5) from the polar hole to the opening 26 and an opening 26 diameter 34. In order to accommodate a plurality of shell 20 sizes, a different insert 50 may be provided having a projection diameter 34 at the required height 33 for each shell 20. However, the insert 50 only needs to contact the shell 20 at the polar hole and at the opening 26 to immobilize the shell 20. Therefore, a single insert 50 can be provided to accommodate a plurality of shell sizes by shaping the outer surface 56 to have the appropriate diameter at the appropriate height for each shell 20 such that the outer surface 56 contour is a function of the size variation of a set of medical devices. In the illustrative case, depending on the shell 20 design and size alternatives, this may result in an insert 50 with a conical outer surface 56 (as shown), a stepped outer surface, a curved outer surface, or some other shape corresponding to the plurality of shells. Providing a single insert 50 that fits a plurality of shells 20 reduces the manufacturing cost of the inserts 50 and simplifies the inventory requirements for the inserts 50.

The top portion 52 of the insert 50 includes a vertical notch 64 formed in each of the four sides of the top portion 52 at the midpoint of each side and a horizontal groove 66 formed in the top portion 52 communicating with each of the notches 64. The notches 64 and grooves 66 receive the retaining clip 100 to prevent the retaining clip 100 from sliding off of the insert 50. The notches 64 and grooves 66 may be sized such that the retaining clip 100 lies flush with or is inset into the top and sides of the insert 50 to better fit within the inner container 150. The vertical notch 64 receives the retaining clip 100 at the edge of the top portion 52 and the horizontal groove 66 receives the retaining clip 100 as it passes horizontally over the top of the insert 50.

The retaining clip 100 includes a base 102 and a pair of opposing support arms 104 that extend upwardly from the base 102 a predefined distance 106. The support arms 104 then bend inwardly and extend toward one another generally parallel to the base 102. The support arms 104 may be connected together in a unitary construct or they may each optionally terminate in one-half of an interlocking closure mechanism 107. In the exemplary embodiment of FIGS. 1-5, the support arms 104 terminate in a closure mechanism 107 having a male half including a disc 108 and a post 110 extending outwardly from the disc 108 and a female half including a ring 112 having an opening 114 for receiving the post 110. The post 110 may snap, press, and/or otherwise fit within the ring 112 to maintain the arms 104 in a closed position. In the illustrative example of FIGS. 1, 4, and 5, the ring 112 receives the post 110 in press-fit relationship. FIG. 4 illustrates the arms in the open position and FIG. 5 illustrates the arms in the closed position. The closure mechanism 107 is offset downwardly from the horizontal portion of the support arms 104 such that the closure mechanism 107 lies within the inner 58 hollow portion of the projection 54 and is flush with or below the horizontal portion of the support arms 104 to allow a flat lid 152 to be sealed over the closure mechanism 107 as shown in FIG. 5.

The base 102 of the retaining clip 100 includes a support pad 116 over which the shell 20 is positioned. The exemplary support pad is in the form of a solid cylinder projecting vertically upwardly from the center of the base 102 toward the closure mechanism and having a longitudinal support pad axis 117. The base 102 further includes a pair of cantilevered springs 118 extending horizontally from the support arms toward the support pad 116 at a height above the support pad such that when a shell 20 is pressed toward the support pad 116, the shell 20 engages the springs 118 and deflects them downwardly. The springs 118 accommodate minor variations in the size of the shell 20, insert 50, and retaining clip 100 and bias the shell 20 against the insert 50 to further immobilize the assembly components relative to one another.

The base 102 and arms 104 are connected by a first web 120 of material that holds the arms 104 and base 102 in a desired angular relationship and help to stiffen the lower part of the retaining clip 100. A second web 122 extends from the first web 120 to the support pad 116 to further stiffen the base 102. The springs 118 originate from these webs 120, 122. The base 102 and lower portions of the arms 104 are thus held in a relatively rigid configuration corresponding to the inside shape of the inner container 150 walls to insure a close fit of the retaining clip 100 in the inner container 150. A pair of fins 124 extend from the arms 104 at right angles to the arms 104 to form cruciform stabilizing surfaces 126 that also abut the inside of the inner container 150 walls to stabilize the retaining clip against rotation within the inner container about the support pad axis.

The retaining clip 100 may be opened and closed by manipulating the closure mechanism 107. Alternatively, the retaining clip 100 may be flexed between an open position and a closed position while the ends of the arms 104 remain connected. The retaining clip 100 may be flexed from a first, closed position in which the insert 50 and medical device are retained to a second, open position in which the insert 50 and medical device may be inserted and removed from the retaining clip 100. The fins 124 provide a convenient location to grasp and squeeze the support arms 104 inwardly toward one another adjacent to the first web 120 to cause the support arms 104 to bow upwardly and outwardly into the second position to facilitate inserting the shell 20 and insert 50 into and removing them from the retaining clip 100. The arms 104 elastically return to the first position when they are no longer squeezed.

The retaining clip 100 may be made of any suitable material and formed by any suitable process. Preferably the retaining clip 100 is made of a lightweight, easily formed, polymer that can withstand common sterilization processes such as gamma irradiation and/or ethylene oxide exposure. The retaining clip 100 may be formed by machining, injection molding, thermoforming, and/or other suitable processes. For example, the exemplary insert of FIGS. 1-5 may be injection molded from high density polyethylene, low density polyethylene, polyethylene terephthalate, and/or other suitable materials.

The inner container 150 includes a bottom 153 and upwardly extending side walls 154 to define an enclosure with an open top 156. The container 150 has a generally rectangular plan form and includes recesses 158 formed in the corners adjacent to the top 156 that receive the snap lugs 53 of the insert 50 in snap-fitting relationship to secure the insert 50 into the inner container 150. The inner container 150 also includes a flat rim 160 against which the sterile barrier lid 152 is sealed. The outer container 170 includes a bottom 173 and upwardly extending walls 174 to define an enclosure with an open top 176. The outer container 170 has a generally rectangular plan form and includes recesses 178 formed in the middle of the side walls 174 adjacent to the top 176 that allow a user to grasp the top edge of the inner container 150 to extract it from the outer container 170. The outer container 170 also includes a flat rim 180 against which the lid 172 is sealed. The inner and outer containers 150, 170 may be made of any suitable material in any suitable process. For example, they may be thermoformed from high density polyethylene, low density polyethylene, polyethylene terephthalate, and/or other suitable materials.

To package an acetabular shell 20, the insert 50 is engaged with the shell 20 and the retaining clip 100 is placed around the insert 50 and shell 20 with the support arms 104 received in the notches 64 and grooves 66 of the insert 50. The retaining clip is secured in place by snapping the closure mechanism 107 into the closed position. Alternatively, the retaining clip may be squeezed to flex the arms and allow the insert and shell to be placed within the retaining clip. The secured assembly can then be handled as an assembled unit without further touching of the shell 20 by grasping the closure mechanism 107, support arms 104, and/or insert 50. The assembly is inserted into the inner container 150 and the snap lugs 53 are snapped into the recesses 158. A lid 152 is sealed to the rim 160 to create a first sterile barrier. The inner container is then placed in the outer container 170 and a lid 172 is sealed to the rim 180 to create a second sterile barrier.

In use, the packaged shell 20 is presented in the operating environment. The outer lid 172 is peeled from the outer container 170. The inner container 150 is grasped by inserting fingers into the recesses 178 in the outer container 170 and grasping the top edge of the inner container 150 and the inner container 150 is extracted from the outer container 170. The inner lid 152 is peeled from the inner container 150. The closure mechanism 107 and/or arms 104 of the retaining clip 100 are grasped and used as a handle to snap the shell 20, insert 50, and retaining clip 100 out of the inner container 150. The assembly can be gripped and manipulated easily without the need to touch the shell 20 itself. The assembly may be placed on a sterile table where the closure 107 may be unsnapped into the open position and the retaining clip 100 and insert 50 removed from the shell 20. Alternatively, the stabilizing fins 124 may be squeezed inwardly by hand pressure to cause the support arms 104 to flex upwardly and outwardly and disengage the notches 64 and grooves 66 in the insert 50 so that the insert 50 and shell 20 may be slid out of the retaining clip 100.

FIG. 6 depicts an alternative arrangement for a retaining clip 200. The retaining clip 200 includes a base 202 and a pair of opposing support arms 204 that extend upwardly from the base 202. The support arms 204 bend inwardly and extend toward one another generally parallel to the base 202. The support arms 204 each terminate in one-half of an interlocking closure mechanism 207. In the exemplary embodiment of FIG. 6, the support arms 204 terminate in a closure mechanism 207 having nesting conical portions. A male portion 208 on one arm 204 presses, snaps, and/or otherwise engages a female portion 214 on the other arm 204 to maintain the arms 204 in a closed position. The base 202 is formed with a cup shaped opening 216 for receiving the shell 20. The retaining clip 200 may be formed of any suitable material in any suitable process. For example the retaining clip 200 may be injection molded from high density polyethylene, low density polyethylene, polyethylene terephthalate, and/or other suitable materials. However, the design of the retaining clip 200 lends itself to economical thermoforming. For example, retaining clip 200 may be advantageously thermoformed from a flexible polyurethane polymer.

In use, the retaining clip 200 is placed around the shell 20 and insert 50 with the arms lying in the notches 64 and grooves 66 in the insert 50 and the closure 207 is secured. The retaining clip 200 retains the shell 20 against the insert 50. Note that with either retaining clip design, 100 or 200, the retaining clip may contact the bottom of the inner container 150, as shown in FIG. 5, or the retaining clip, 100 or 200, may be suspended above the bottom of the inner cavity 150.

Although embodiments of a medical package and its use have been described and illustrated in detail, it is to be understood that the same is intended by way of illustration and example only and is not to be taken by way of limitation. Accordingly, variations in and modifications to the package and its use will be apparent to those of ordinary skill in the art, and the following claims are intended to cover all such modifications and equivalents.

What is claimed is:

1. A package for a medical device, the package comprising:
   a container defining a cavity with surrounding cavity walls and an opening;
   an insert releasably engaged with the medical device to constrain the position of the medical device relative to the insert, the insert engaging the container to constrain the position of the medical device relative to the container; and
   a retaining clip having a base engaging the medical device and support arms extending from the base and encircling the insert to secure the insert in engagement with the medical device.

2. The package of claim 1 wherein one of the insert and retaining clip engage the cavity opening to at least partially close the opening.

3. The package of claim 2 wherein the insert engages the opening in snap-fitting relationship to secure the insert relative to the cavity walls.

4. The package of claim 1 wherein the insert, retaining clip, and medical device form a secure assembly insertable into and removable from the cavity as an assembled unit.

5. The package of claim 4 wherein the retaining clip defines a handle for gripping and manipulating the assembly.

6. The package of claim 1 wherein the retaining clip further comprises a closure operable to secure the retaining clip in a closed position.

7. The package of claim 6 wherein the closure further comprises a male portion on a first arm and a female portion on a second arm, the male and female portions being engageable to close the retaining clip and the male and female portions being separable to open the retaining clip.

8. The package of claim 1 wherein the retaining clip further comprises at least one spring engaged with the medical device to bias the medical device into contact with the insert.

9. The package of claim 1 wherein the medical device has a height and a width and the insert includes a portion with a height and a width, the width of the portion varying along its height such that a single insert is interchangeably engageable with a plurality of different medical devices having different heights and widths.

10. The package of claim 1 wherein the support arms are elastically deformable from a first position in which the retaining clip secures the insert and medical device to a second position in which the insert and medical device may be inserted and removed from the retaining clip, the arms returning to the first position in the absence of external force.

11. The package of claim 1 wherein the support arms are responsive to being squeezed by a user's hand to elastically deform from a first position in which the retaining clip secures the insert and medical device to a second position in which the insert and medical device may be inserted and removed from the retaining clip, the arms returning to the first position when they are no longer squeezed.

12. A package for an acetabular shell component of a hip joint prosthesis, the shell having an outer surface, an inner surface, an equatorial opening and a polar hole communicating with the inner surface, the package comprising:
    a first container having a bottom and upwardly extending side walls defining a cavity with an open top;
    an insert having a top portion releasably engaged with the open top of the container, the insert further comprising a projection extending downwardly from the top portion to engage the shell, the projection having an outer surface engaged with the equatorial opening and an end portion engaged with the polar hole; and
    a retaining clip having a base supporting the shell and support arms extending upwardly from the base and encircling the insert to secure the insert in engagement with the shell.

13. The package of claim 12 wherein the outer surface of the projection is conical and the end portion of the projection is cylindrical.

14. The package of claim 12 wherein the shell has a height from the polar hole to the equatorial opening and the equatorial opening has a width, the outer surface of the projection having a height and a width, the width of the outer surface varying along its height such that a single inset is interchangeably engageable with a plurality of different shells having different heights and opening widths.

15. The package of claim 12 wherein the top portion of the insert includes notches in its edges for receiving the support arms of the retaining clip.

16. The package of claim 15 wherein the top portion includes a top surface defining grooves for receiving the supports arms of the retaining clip, the grooves communicating with the notches.

17. The package of claim 12 wherein the top portion engages the open top of the container in snap fitting relationship.

18. The package of claim 12 wherein the retaining clip further comprises at least one spring extending from the retaining clip to engage the shell and bias the shell into contact with the insert.

19. The package of claim 12 wherein the insert, retaining clip, and shell form a secure assembly insertable into and removable from the container as an assembled unit.

20. The package of claim 19 wherein the retaining clip defines a handle for gripping and manipulating the assembly.

21. The package of claim 12 wherein the retaining clip further comprises a closure operable to secure the retaining clip in a closed position.

22. The package of claim 21 wherein the closure further comprises a post extending from a first arm and a ring formed on a second arm, the post being receivable by the ring to close the retaining clip.

23. The package of claim 21 wherein the projection is hollow and open at the top portion, the closure overlying the top portion and being offset downwardly into the hollow projection.

24. The package of claim 12 wherein the support arms are elastically deformable from a first position in which the retaining clip secures the insert and medical device to a second position in which the insert and medical device may be inserted and removed from the retaining clip, the arms returning to the first position in the absence of external force.

25. The package of claim 12 wherein the shell further comprises tabs projecting outwardly adjacent the equatorial opening and the projection includes elongated grooves for receiving the tabs.

26. The package of claim 12 wherein the support arms each further comprise a fin extending from the arm at right angles to the arm to form a cruciform stabilizing surface.

27. The package of claim 12 further comprising a second container, the first container nesting inside of the second container, the first container being sealed with a first sterile barrier and the second container being sealed with a second sterile barrier.

* * * * *